(12) United States Patent
Engelbrecht et al.

(10) Patent No.: US 7,625,442 B2
(45) Date of Patent: Dec. 1, 2009

(54) SHAPED BODIES THAT CAN BE SCANNED BY OPTICAL SYSTEMS

(75) Inventors: Juergen Engelbrecht, Hamburg (DE); Wolfram Ziegler, Hamburg (DE); Andreas Sprafke, Hamburg (DE)

(73) Assignees: S & C Polymer Silicon- und Composite-Spezialitäten GmbH, Elmshorn (DE); R-Dental Dentalerzeugnisse GmbH, Hamburg (DE)

( * ) Notice: Subject to any disclaimer, the term of this patent is extended or adjusted under 35 U.S.C. 154(b) by 670 days.

(21) Appl. No.: 10/343,527

(22) PCT Filed: Aug. 3, 2001

(86) PCT No.: PCT/EP01/09018

§ 371 (c)(1), (2), (4) Date: Apr. 24, 2003

(87) PCT Pub. No.: WO02/11678

PCT Pub. Date: Feb. 14, 2002

(65) Prior Publication Data

US 2003/0162150 A1 Aug. 28, 2003

(30) Foreign Application Priority Data

Aug. 3, 2000 (DE) ................................ 100 38 564

(51) Int. Cl.
*C09K 3/00* (2006.01)
(52) U.S. Cl. .................. 106/35; 106/623; 106/626; 106/640; 106/641; 106/642; 106/733; 106/814; 523/115; 523/116
(58) Field of Classification Search .............. 523/115, 523/116; 106/35, 623, 626, 640, 641, 642, 106/733, 814
See application file for complete search history.

(56) References Cited

U.S. PATENT DOCUMENTS

| 4,219,520 A | * | 8/1980 | Kline .................. 264/129 |
| 4,527,979 A | * | 7/1985 | McLean et al. ........... 433/228 |
| 4,713,403 A | * | 12/1987 | Yoshida et al. .......... 523/115 |
| 5,084,491 A | * | 1/1992 | Kerby .................. 523/116 |
| 5,189,077 A | * | 2/1993 | Kerby .................. 523/116 |
| 5,189,077 A | * | 6/1996 | Kerby .................. 523/116 |
| 6,103,800 A | * | 8/2000 | Peterson et al. .......... 524/296 |
| 6,270,562 B1 | * | 8/2001 | Jia ..................... 106/35 |
| 6,880,296 B1 | * | 4/2005 | Engelbrecht et al. .......... 52/25 |

FOREIGN PATENT DOCUMENTS

| EP | 0 311 214 A | | 4/1989 |
| GB | 2257433 A | * | 1/1993 |
| JP | 25003738 | * | 10/1950 |
| JP | 07025720 | * | 1/1995 |
| JP | 09323912 | * | 12/1997 |
| WO | WO 01/13814 A | | 3/2001 |
| WO | WO 01/13815 A | | 3/2001 |

OTHER PUBLICATIONS

"Properties of a thromboresistant surgically useful composite material based on polysiloxane rubber and graphite", Zamyslov et al., Zhurnal Priklandnoi Khimii (Santkt-Peterburg) 1997, 70(7), 1212-1214. Abstract only.*

"Antimicrobal properties of a zinc oxide phosphate cement and a glass ionomer cement with and without silver additives", Schmalz, Deutsche Zahnaerztliche Zeitschrift (1987), 42(7), 628-32. Abstract only.*

"Effect of 5% sodium hypochlorite or Tubulicid pretreatment in vivo on the marginal adaptation of dental adhesives and glass ionomer cemetns", Van Dijken et al., Dental Materials (1 987), 3(6), 303-6. Abstract only.*

* cited by examiner

*Primary Examiner*—Paul Marcantoni
(74) *Attorney, Agent, or Firm*—Frommer Lawrence & Haug, LLP; Ronald R. Santucci

(57) ABSTRACT

The invention relates to a kit of parts consisting of: a) a material for producing a shaped body; b) a metal powder, a powder of a metal alloy, a powder of a pigment having a metallic effect or a powder having a laminar structure, and; c) if needed, of customary additives. The inventive kit of parts can be used to produce shaped bodies, especially in the field of dentistry, which can be excellently detected by optical systems.

20 Claims, No Drawings

SHAPED BODIES THAT CAN BE SCANNED BY OPTICAL SYSTEMS

This application is a 371 of PCT/EP01/09018 filed on Aug. 3, 2001, published on Feb. 14, 2002 under publication number WO 02/11678 A2 which claims priority benefits from German patent application number DE 100 38 564.8 filed Aug. 3, 2000.

This invention relates to a kit of parts, comprising
a) a material for producing a shaped body,
b) a metal powder, a powder of a metal alloy, a powder of a pigment having a metallic effect or a powder having a laminar structure, and
c) optionally conventional additives.

These kits of parts are suitable for optical detection of morphologies and geometries of shaped bodies with subsequent reproduction of same by CAD/CAM systems. This invention relates in particular to kits of parts for producing models or to materials for producing impressions, especially in the fields of dentistry and medicine.

Optical detection of morphologies and geometries of shaped bodies with subsequent reproduction of these shapes by CAD/CAM systems is essentially known. However, in photographic detection (e.g., with infrared or visible light) and in optical scanning (e.g., with laser beams), the optical behavior of the materials is not enough to obtain adequate information for accurate reproduction of all morphological details. It is especially difficult to detect edges per se and unfavorable angular positions.

For example, it is usually difficult or impossible to optically "read" the surface of the plaster of Paris impressions which are widely prepared in the field of dentistry. There has been no lack of attempts to improve the readability of such plaster of Paris. For example, German Patent 195 48 655 has disclosed the addition of large amounts of pigments to these plaster of Paris impressions to improve the reflection behavior. However, these modifications did not constitute an adequate improvement for the practice of optical reproduction of models by CAD/CAM systems.

A definite step on the way to accurate reproducibility of morphologies and geometries of shaped bodies has been achieved by direct application of powdered pigments to the surfaces to be detected optically (Cerec liquid/Cerec powder, VITA or ProCAD adhesive medium/ProCAD contrast powder, Ivoclar). In this method, the surface is first provided with an adhesive, and then a white powder is distributed finely on it. Then the surface can be detected with adequate surface coverage, almost regardless of the angle of incidence, by using both photographic systems and laser systems. One disadvantage, however, is the distortion due to the additional spatial presence of adhesive/powder per se as well as distortion due to unequal layer thicknesses (snowdrift effect). In addition, there is increased preparation time, which is not irrelevant.

The object of the present invention was therefore to provide shaped bodies and/or means for producing shaped bodies with which it is possible to accurately scan or detect the shaped bodies optically so that they can then be reproduced with CAD/CAM systems.

According to this invention, this object has been achieved by a kit of parts comprising
a) a material for producing a shaped body,
b) a metal powder, a powder of a metal alloy, a powder of a pigment having a metallic effect or a powder having a laminar structure, and
c) optionally conventional additives.

Shaped bodies produced with this kit of parts can be detected photographically and/or scanned optically by essentially conventional optical systems and reproduced by CAD/CAM systems.

In particular, the kit of parts according to this invention can be characterized in that components a) and b) are present in the form of a mixture.

The chemical nature of the materials according to this invention, in particular curable compounds, which should lead to the desired shaped bodies to be duplicated, may differ greatly, depending on the intended application. In principle, starting materials which are capable of forming a body having a defined shaped are suitable.

Materials suitable for producing dental shaped bodies are preferred. Such materials a) may also be present as components $a_1) \ldots a_n)$ in the kit of parts, preferably as components $a_1)$ and $a_2)$, which are combined and react together in the production of the shaped bodies. For example, these may be polymerizing systems, polyadditive systems or polycondensing systems.

In the production of rigid shaped bodies for the purpose of optical detection or scanning, in particular in the production of dental models, conventional materials may be used as the basis for the materials according to this invention. Such conventional materials include, for example, plaster, in particular hard plaster, cast resins such as epoxy resins or polyurethanes; cements such as dental silicate cements or glass ionomer cements, filled or unfilled methacrylate systems such as dental filling composites or temporary crown and bridge materials, ceramic mixtures, hard waxes or thermoplastics may also be used as the basis for the materials according to this invention.

In the production of elastic shaped bodies, for example, the conventional materials are indicated as the starting basis, and they include soft elastic materials or hard elastic materials for cast impressions. Examples of this type include condensation-crosslinking silicones or addition-crosslinking silicones, polyethers, polysulfides, alginates or hydrocolloids, such as those used in the field of dentistry in particular.

The starting materials mentioned above are modified to yield the products according to this invention by adding metal powders and/or powders of metal alloys and/or pigments having a metallic effect and/or powders having laminar structures to the starting materials. Especially good results are achieved when the additives are incorporated intimately and homogeneously.

All powders of metals and metal alloys are suitable if they are chemically compatible with the respective base materials. Examples include gold, silver, platinum, palladium, copper, titanium, alloys such as bronzes or brass. Because of their low density (and possibly also more favorable sedimentation behavior and more favorable price) metals such as aluminum, magnesium and alloys thereof are especially suitable. It is important for these metals to be present in a sufficiently fine particle size and to have a particle shape (e.g., a flattened form or flakes) that is favorable for light reflection. The powders may also advantageously be in a surface-coated form.

Suitable pigments having a metallic effect include those which, when added to a mixture, can result in a metallic appearance, although they are not metals themselves. Pigments of this type include pigments having reflective laminar structures such as coated or uncoated mica pigments, for example.

Suitable powders having a laminar structure include, for example, graphite or molybdenum sulfide.

The preferred average particle sizes of these powders are those less than 100 µm. Especially preferred average particle sizes are those less than 20 μm. Powders with average particle sizes of less than 5 μm are most especially preferred.

The flake shape is an especially preferred shape for the metallic powders, powders of metal alloys, pigments having a metallic effect or powders having a laminar structure.

Thus, the metal powder, the powder of a metal alloy, the powder of a pigment having a metallic effect or the powder having a laminar structure may have, for example, more than 50 percent by weight lamellar structures, preferably more than 70 percent by weight and even more preferably more than 90 percent by weight lamellar structures.

According to this invention, components a) and b) may be present in a ratio of 99.8:0.2 percent by weight to 60:40 percent by weight, preferably in a ratio of 98:2 percent by weight to 90:10 percent by weight.

Modification of the starting materials listed above with the additives of metal powders or pigments having a metallic effect or powders having a laminar structure leading to the materials according to this invention as described above makes it possible to produce shaped bodies which permit in an excellent manner photographic and/or optical detection or scanning even at the least favorable angular positions. An additional surface treatment with surface powders is then no longer necessary. The information measured is accurate enough to manufacture a reproduced body shape with the help of a CAD/CAM system based on copying, milling and grinding methods.

The term reproduction is understood to include not only a 1:1 reproduction with respect to the optically measured shaped body but also a shaped body that is reduced, enlarged or inverted (negative to positive or the like) by data transformation. The number of reproductions produced in this way may be unlimited.

Components c) may include, for example, the conventional fillers, conventional pigments or coloring agents, stabilizers, thixotropy agents, emulsifiers, suspension aids or sedimentation-preventing additives. In particular when the material has a very low viscosity, it is advantageous to use additives that prevent sedimentation.

Furthermore, shaped bodies made available according to this invention can be produced by using a kit of parts. To produce a shaped body, components a), b) and optionally c) are mixed together, and the mixture is shaped, in which case the mixture can be shaped by casting in a mold, for example.

Thus, a kit of parts according to this invention may be used for producing shaped bodies, in particular for producing shaped bodies for use in the field of dentistry, in particular for modeling of dental preparations.

The following examples are presented to illustrate this invention.

COMPARATIVE EXAMPLE 1

To produce an inlay with the help of a Cerec 3 device from the company Sirona in Germany, which may be accomplished directly and in a time-saving manner in the dentist's office (chair side), an alginate impression is prepared of the lower jaw, which includes a molar tooth with a MOD cavity preparation. The alginate impression impression is cast using a beige addition-crosslinking model silicone ("chair side in a minute, wash material" from the company Roydent, USA) and after hardening, the cavity is measured with a Cerec 3 Scan.

The message appears: "The optical properties of the surface are inadequate."

Although the hard silicone model is sufficient to create a composite inlay by the direct method using composite filling material, it is not sufficient for scanning the cavity and causing the proper inlay to be milled from a dental ceramic block with the help of the CAD/CAM system Cerec 3 method.

COMPARATIVE EXAMPLE 2

Comparative Example 1 is repeated, but this time before casting the cavity situation of the alginate impression, 2.0% titanium dioxide pigment is added to the model silicone. The line image of the Cerec 3 Scan is improved, but it still has so many "misses" that it is impossible to produce the inlay.

EXAMPLE 1

According to this Invention

Comparative Example 1 is repeated again, but this time, before casting the cavity situation of the alginate impression, 2.0% aluminum powder pigment is added to the model silicone; the pigment particles in this powder are approximately 10 μm in size and have a lamellar structure. The measurement is performed in advance as described in Examples 1 and 2. The line image of the Cerec 3 Scan is very good and shows hardly any misses, and if so they are very small, the images very good and there is only slight overswing at the edges, and even steep flanks are imaged very well on both sides of the elongated cavity.

Accurate optical detection can be performed with the help of the Cerec 3 Scan, and an inlay that fits accurately can be produced by milling.

EXAMPLE 2

According to this Invention

Comparative Example 1 is repeated again, but this time before casting the cavity situation of the alginate impression, 5.0% copper-zinc alloy powder is added to the addition-crosslinking model silicone; the pigment particles in this powder are approximately 8 μm in size. A measurement is performed as described in Examples 1 and 2. The line image of the Cerec 3 Scan is good. The image is definitely improved.

EXAMPLE 2a

According to this Invention

Comparative Example 1 is repeated again, but this time before casting the cavity situation of the alginate impression, 1.5% fine graphite powder is added to the addition-crosslinking model silicone. The measurement is performed as in the preceding examples. The line image of the Cerec 3 Scan is very good and contains virtually no errors, and the steep flanks of the cavity are imaged by multiple points.

COMPARATIVE EXAMPLE 3

An attempt is made to obtain an optical reproduction with Cerec 3 of the structure of a polyether impression cast (material Impregum F, Espe, Germany). Apart from the fact that only approximately 5% of the surface can be reproduced at all, only partial walls and no surfaces appear on these few surfaces. This material is not suitable for optical scanning.

EXAMPLE 3

According to this Invention

In preparing the paste, 3.0% aluminum powder from Example 3 is added to Impregum F.

A very good line image with only a few misses is obtained; the image is very good and all planes are imaged well.

COMPARATIVE EXAMPLE 4

An attempt is made to optically survey structural parts of an alginate impression (Alginmax) using Cerec 3.

The device reports that the optical properties are inadequate and it does not continue performing measurements.

EXAMPLE 4

According to this Invention

Using the same alginate, now mixed with 5.0% coarser aluminum powder (25 µm particle size) parts are again molded and again measured optically. Line images with only approximately 2% defects are obtained, and the imaging results are good. Even in the case of the alginate, the addition of the metal powder improves the optical properties significantly.

COMPARATIVE EXAMPLE 5

A white modelling plaster (Gilstone) is processed to yield a model, which is measured optically.

This yields a line image full of defects. This data is not suitable for analysis.

EXAMPLE 5

According to this Invention

In contrast with Comparative Example 5, 2.5% aluminum powder (25 µm) is added here to the Gilstone plaster. The plaster prepared with water yielded the desired model. The line image is practically free of errors, and the imaging is very good. Even a repetition with only 1% aluminum powder still yields almost equally good results.

EXAMPLE 6

According to this Invention

As in Example 5, 5.0% titanium dioxide-coated mica (particle size less than 15 µm) was added to the Gilstone plaster. The line image shows slightly more misses than that of Example 5, but the imaging is good.

The invention claimed is:

1. A kit of parts comprising a) a material for producing a shaped body to be used as a model in the field of dentistry or medicine, b) a metal powder, a powder of a metal alloy, a powder of a pigment having a metallic appearance or a powder having a laminar structure, wherein the average particle size of these powders is less than 100 µm and the particle shapes are flakes or a flattened form favorable for light reflection, and c) optionally additives, whereby the morphologies and geometries of the shaped body are optically detectable in a manner suitable for CAD/CAM applications.

2. The kit of parts according to claim 1, characterized in that components a) and b) are present in the form of a mixture.

3. The kit of parts according to any one of the preceding claims, characterized in that the material is a curable material.

4. The kit of parts according to any one of the preceding claims, characterized in that the material is a material for producing shaped bodies for use in dentistry.

5. The kit of parts according to any one of the preceding claims, characterized in that the material is a plaster, a casting resin, cement, methacrylate system, wax, thermoplastic, a ceramic mixture, a condensation-crosslinking or addition-crosslinking silicone, a polyether, polysulfide, alginate or hydrocolloid or a mixture thereof.

6. The kit of parts according to any one of the preceding claims, characterized in that the casting resin is an epoxy resin or a polyurethane resin.

7. The kit of parts according to any one of the preceding claims, characterized in that the cement is a dental silicate cement or a glass ionomer cement.

8. The kit of parts according to any one of the preceding claims, characterized in that the methacrylate system is a filled or unfilled system.

9. The kit of parts according to any one of the preceding claims, characterized in that the material is a dental filling composite or a temporary crown or bridge material.

10. The kit of parts according to any one of the preceding claims, characterized in that the metal powder includes gold, silver, platinum, palladium, copper, tin, zinc, titanium, aluminum, or magnesium.

11. The kit of parts according to any one of the preceding claims, characterized in that the powder of a metal alloy includes alloys of gold, silver, platinum, palladium, copper, tin, zinc, titanium, aluminum, or magnesium as well as brass or bronze.

12. The kit of parts according to any one of the preceding claims, characterized in that the pigment having a metallic appearance is a coated or uncoated mica pigment.

13. The kit of parts according to any one of the preceding claims, characterized in that the powder having a laminar structure consisting of graphite or molybdenum sulfide.

14. The kit of parts according to any one of the preceding claims, characterized in that a) and b) are present in a ratio of 99.8:0.2 percent by weight to 60:40 percent by weight.

15. The kit of parts according to any one of the preceding claims, characterized in that components a) and b) are present in a ratio of 99:1 percent by weight to 90:10 percent by weight.

16. The kit of parts according to any one of the preceding claims, characterized in that the metal powder, the powder of a metal alloy or the powder of a pigment having a metallic appearance comprises lamellar structures more than 50 percent by weight of said powder.

17. The kit of parts according to any one of the preceding claims, characterized in that the metal powder, the powder of a metal alloy or the powder of a pigment having a metallic appearance comprises lamellar structures more than 70 percent by weight of the total composition of the kit of parts.

18. The kit of parts according to any one of the preceding claims, characterized in that the metal powder, the powder of a metal alloy or the powder of a pigment having a metallic appearance comprises lamellar structures more than 90 percent by weight of the total composition of the kit of parts.

19. The kit of parts according to any one of the preceding claims, characterized in that the average particle size of the metal powder, the powder of a metal alloy or the powder of a pigment having a metallic appearance amounts to up to 20 µm.

20. The kit of parts according to any one of the preceding claims, characterized in that the average particle size of the metal powder, the powder of a metal alloy or the powder of a pigment having a metallic appearance amounts to up to 5 µm.

* * * * *

UNITED STATES PATENT AND TRADEMARK OFFICE
CERTIFICATE OF CORRECTION

PATENT NO. : 7,625,442 B2  Page 1 of 1
APPLICATION NO. : 10/343527
DATED : December 1, 2009
INVENTOR(S) : Engelbrecht et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1058 days.

Signed and Sealed this

Second Day of November, 2010

David J. Kappos
*Director of the United States Patent and Trademark Office*